United States Patent [19]

Vincent et al.

[11] Patent Number: 5,164,414

[45] Date of Patent: Nov. 17, 1992

[54] USE OF N-MYRISTOYL-(S)-PHENYLALANINE FOR THE TREATMENT OF DISEASES INVOLVING MYRISTOYLATION

[75] Inventors: Michel Vincent, Bagneux; Georges Remond, Versailles; Yolande Herve, Puteaux; Jean-Albert Boutin, Suresnes, all of France

[73] Assignee: Adir Et Compagnie, Courbevoie, France

[21] Appl. No.: 645,124

[22] Filed: Jan. 24, 1991

[30] Foreign Application Priority Data

Jan. 25, 1990 [FR] France .................... 90 00834

[51] Int. Cl.$^5$ ............................ A61K 31/195
[52] U.S. Cl. .................... 514/563; 514/564
[58] Field of Search .................. 514/563, 564

[56] References Cited

U.S. PATENT DOCUMENTS 4,778,877 10/1988 Adams et al. ................ 530/328
4,778,878 10/1988 Adams et al. ................ 530/328

OTHER PUBLICATIONS

CA76(20):117436j Shimizu et al., 1972.

*Primary Examiner*—Frederick E. Waddell
*Assistant Examiner*—Russell Travers
*Attorney, Agent, or Firm*—Gordon W. Hueschen

[57] ABSTRACT

The invention relates to the use of N-myristoyl-(S)-phenylalanine in the treatment of diseases involving myristoylation such as cancer or AIDS.

Medicinal products including N-myristoyl-(S)-phenylalanine which are effective for such purpose.

3 Claims, No Drawings

USE OF N-MYRISTOYL-(S)-PHENYLALANINE FOR THE TREATMENT OF DISEASES INVOLVING MYRISTOYLATION

The present invention relates to the use of N-myristoyl-(S)-phenylalanine as an inhibitor of N-myristoyltransferase (NMT).

It is known from the prior art that the N-terminal amino group of proteins is blocked by acetyl, pyroglutamyl and formyl groups. Now, SHOJI et al. have demonstrated that myristic acid was linked via a covalent bond to the N-terminal group of the catalytic subunits of cyclic AMP-dependent protein kinase (Proc. Natl. Acad. Sci. USA, (1982), 79, 6123–6131).

The existence of this terminal myristoyl group has been shown since then in various other proteins, such as calcineurin B (AITKEN et al., Febs Letters, (1982) 150, No. 2, 314–318) or tyrosine protein kinase (TPK) (BUSS and SEFTON, J. Virol, (1985), 53, 7–12).

In the oncogene field as well, BISHOP demonstrated that a transforming protein underwent a myristoylation during maturation. Moreover, it has since been shown that this maturation step, proceeding via a myristoylation, was essential to the transforming power of this protein (KAMPS, BUSS and SEFTON, Proc. Natl. Acad. Sci. USA, (1985), 82, 4625–4628). This concept has been generalized since then to a large number of other transforming proteins of viral origin (RHEE and HUNTER, J. Virol., (1987), 61, 1045–1053). This maturation is catalyzed by an enzyme known as N-myristoyltransferase, demonstrated by TOWLER and GLASER (Proc. Natl. Acad. Sci, USA, (1986), 83, 2812–2816).

Now, NMT in practice recognizes, on the one hand as a cosubstrate only myristic acid, and on the other hand as a substrate proteins containing a glycine as the last amino acid on the N-terminal side, with participation of the peptide sequence adjoining this glycine (participation of 7 amino acids).

Thus, myristoylation of the N-terminal glycine residue of some proteins plays a very important part in some mechanisms participating in cell transformation and the control of cell proliferation. It has, moreover, been shown by SHOJI et al. (Japanese Patents JP 63-146,851, JP 62-255,810 and JP 62-126,384) that myristoylglycine or oligopeptide derivatives possessed an inhibitory effect against cell transformation or proliferation or retrovirus multiplication.

The invention consists more especially in the use of N-myristoyl-(S)-phenylalanine as an inhibitor of the myristoylation of proteins such as gag by means of the enzyme responsible for this myristoylation, that is to say N-myristoyltransferase.

Inhibition of the activity of this enzyme by this compound had never hitherto been demonstrated. In addition, the use of N-myristoyl-(S)-phenylalanine as an inhibitor of NMT leads to a markedly greater inhibition of the activity of this enzyme than the use of compounds described in the prior art as inhibitors of the proliferation of cancer cells and retroviruses.

In effect, a detailed study of the influence exerted by N-myristoyl-(S)-phenylalanine on cell proliferation and transformation was carried out using cancer cells of murine origin (L 1210). After extraction of the enzyme from this biological medium and measurement of its activity, it is apparent that the addition of N-myristoyl-(S)-phenylalanine strongly inhibits its activity.

In addition, this compound displays cytotoxic activity against cancer cells in culture, such as L 1210 (of murine origin) or HL 60 (of human origin). This cytotoxicity has proved to be markedly greater than that due to N-myristoylglycine on these cells.

Thus, this inhibition of activity is all the more advantageous for the fact that this enzyme plays a dominant part, especially in the maturation either of transforming proteins involved in some cancers, or of proteins which are themselves involved in retrovirus maturation.

N-Myristoyl-(S)-phenylalanine hence has potential applications in the treatment of cancer and/or retrovirus diseases such as AIDS.

The subject of the present invention is also the use of N-myristoyl-(S)-phenylalanine, or one of its addition salts with a pharmaceutically acceptable base, in the form of a pharmaceutical composition, alone or in combination with one or more non-toxic, inert excipients or vehicles.

Among pharmaceutial compositions according to the invention, there may be mentioned those which are suitable for oral, parenteral or nasal administration, simple or sugar-coated tablets, sublingual tablets, sachets, packets, hard gelatin capsules, sublingual preparations, troches, suppositories, and the like.

The dosage varies according to the patient's age and weight, the nature and severity of the condition and also the administration route. The latter may be oral, nasal, rectal or parenteral. Generally speaking, the unit dosage ranges between 0.1 and 100 mg for a treatment taken in 1 to 3 doses per 24 hours.

The examples which follow illustrate the invention but in no way limit the latter.

EXAMPLE 1

Synthesis of N-myristoyl-(S)-phenylalanine

Stage A: tert-Butyl N-myristoyl-(S)-phenylalaninate

Using the technique described by VAUGHN, J. R. jr. and OSATO, R. L. (JACS, (1951), 73, 5553), the expected product is obtained from myristic acid and tert-butyl (S)-phenylalaninate.

Yield: 92%.

Stage B: N-Myristoyl-(S)-phenylalanine 2 g of the compound obtained in stage A are dissolved in 25 ml of dichloromethane. After the addition of 5 ml of trifluoroacetic acid, the solution is left for 24 hours at room temperature. It is then evaporated to dryness. The expected product is obtained after crystallization of the residue in pentane and filtration.

Yield: 49%

Melting point (Kofler): 74° C.

Elemental microanalysis:

|  | C % | H % | N % |
|---|---|---|---|
| calculated: | 73.56 | 9.93 | 3.73 |
| found: | 73.30 | 9.81 | 3.58 |

PHARMACOLOGICAL STUDY

EXAMPLE 2

Method for inhibiting N-myristoyltransferase (NMT) by analogs of the product of the reaction which it catalyzes Stage A: Bulk culture of L 1210 cancer cells Leukemic cells of murine origin (L 1210) are cultured in 500- to 1000-ml roller bottles in a medium comprising: RPMI 1640 medium (Gibco); 10% fetal calf serum; 50 units/ml of penicillin; 50 μM streptomycin; 2 mM glutamine; and 10 mM HEPES (Gibco). The cells grow with continuous agitation at 37° C. in an atmosphere of 5% $CO_2$/95% air. The cells are collected and washed. The final pellet, typically containing $2.5 \times 10^{11}$ cells is resuspended in a lysis buffer [50 mM Tris, pH 7.9; 1 mM DTT; 1 mM EDTA; and 250 mM sucrose]. The cells are lysed and homogenized. The microsomes (vesiculated endoplasmic reticulum) are collected by centrifugation at 105,000 g as a pellet.

Stage B: Solubilization of the enzyme from this biological source

NMT is a membrane enzyme. To solubilize this enzyme, this suspension is then diluted to ⅔ in a solubilization buffer [50 mM HEPES, pH 7.5, 1 mM EDTA, 1 mM DTT, 10% glycerol and 3% Triton 770] and maintained for 30 min at 4° C. with stirring. This suspension is then centrifuged again at 105,000 g for 75 min. The material insoluble in the detergent sediments as a pellet. The supernatant comprises the whole of the NMT activity present in the L 1210 microsomes.

Stage C: Measurement of the N-myristoyltransferase activity and of its inhibition by N-myristoyl-(S)-phenylalanine The compounds are then tested on the supernatant in competition with the peptide substrate Gly-Asn-(Ala)$_4$-(Arg)$_2$ ("G8R") according to the conditions which follow, as described by TOWLER et al. (PNAS, (1987), 84, 2708-2711). Myristoylcoenzyme A is synthesized enzymatically immediately before use by incubation of myristate with ATP, Coenzyme A (lithium salt) and Pseudomonas Acyl-Coa synthetase (20 min at 30° C.). The peptide substrate and the biological source as obtained above are then added. The mixture is incubated for 10 min at 37° C.; the reaction is then stopped with 110 μl of methanol and 10 μl of trichloroacetic acid. The medium is left at 4° C. for 10 min and then centrifuged at 10,000 g for 5 min. An aliquot (30 μl) of the final supernatant is injected into an HPLC system equipped with a μBondapak column (Waters) and developed with a linear gradient as described by Towler et al. (PNAS, (1987), 84, 2708-11). Detection of the acylated peptide is performed using a radioactive line detector (Berthold) by means of the addition of 5 ml/min of scintillation fluid (Zinsser). The acylated peptide is eluted at 85% acetonitrile-TFA/15% H20-TFA.

The compounds tested as inhibitors are suspended in a 0.1% solution of Triton 770 after a brief sonication in the cold state. 10 μl of the solution of inhibitor are added to the reaction medium. The experimental conditions are identical to those described above. The activity of the compound is evaluated on the basis of the decrease in control activity, incubated under the same conditions but in the presence of the solution of suspension.

Under these conditions, N-myristoyl-(S)-phenylalanine possesses an $IC_{50}$ equal to $2 \times 10^{-4}$ M. This corresponds to an activity 15-fold greater than that measured for N-myristoylglycine, the $IC_{50}$ of which is equal to $3 \times 10^{-3}$ M.

EXAMPLE 3

Cytotoxicity

The cytotoxicity of the compounds is assessed using the calorimetric test described by ALLEY et al. (Cancer Res., (1988) 48, 589-601). This automated test is routinely used on 2 cell lines: L 1210 (mouse leukemia) and HL 60 (human promyelocyte). On each of these lines, the cytotoxicity is assessed using 9 concentrations of the compounds. The $IC_{50}$ is the concentration inhibiting 50% of cell growth.

The results are collated in the following table:

|  | $IC_{50}$ (M) on L 1210 cells | $IC_{50}$ (M) on HL 60 cells |
|---|---|---|
| N-Myristoyl-(S)-phenylalanine | 29.5 | 12.8 |
| N-Myristoyl-glycine | 48.4 | 20.5 |

These results show that N-myristoyl-(S)-phenylalanine displays markedly greater cytotoxicity than N-myristoylglycine

PHARMACEUTICAL COMPOSITION

EXAMPLE 4

Tablet: Preparation formula for 1000 tablets containing a 2-mg dose of active principle

| N-Myristoyl-(S)-phenylalanine | 2 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A method for treating an animal or human living body afflicted with a cancer susceptible to treatment by inhibition of N-myristoyltransferase, consisting essentially of the step of administering to the said living body an effective tumor-inhibitory amount of N-myristoyl-(S)-phenylalanine or an addition salt thereof with a pharmaceutically-acceptable base.

2. The method of claim 1 wherein the N-myristoyl-(S)-phenylalanine is administered in the form of a pharmaceutical composition thereof in which it is present together with a pharmaceutically-acceptable carrier or diluent.

3. The method of claim 1 wherein the N-myristoyl-(S)-phenylalanine is administered by the oral route.

* * * * *